(12) United States Patent
Han et al.

(10) Patent No.: US 7,842,305 B2
(45) Date of Patent: *Nov. 30, 2010

(54) METHOD OF PREPARING BIODEGRADABLE DUAL PORE POLYMER SCAFFOLDS FOR TISSUE ENGINEERING

(75) Inventors: Dong Keun Han, Seoul (KR); Kwang-Duk Ahn, Seoul (KR); Hyun Jung Jung, Seoul (KR); Kwideok Park, Yongin-si (KR)

(73) Assignee: Korea Institute Of Science And Technology, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 11/526,280

(22) Filed: Sep. 21, 2006

(65) Prior Publication Data

US 2007/0092557 A1 Apr. 26, 2007

(30) Foreign Application Priority Data

Oct. 25, 2005 (KR) .................. 10-2005-0100632

(51) Int. Cl.
*A61F 2/00* (2006.01)
(52) U.S. Cl. ..................................... 424/426
(58) Field of Classification Search ........... None
See application file for complete search history.

(56) References Cited

U.S. PATENT DOCUMENTS

| 5,223,246 | A | * | 6/1993 | Kondo et al. ............ 424/44 |
| 5,723,508 | A |   | 3/1998 | Healy et al. |
| 6,562,374 | B1 | * | 5/2003 | Han et al. ............ 424/484 |
| 2006/0147486 | A1 |   | 7/2006 | Kim et al. |

FOREIGN PATENT DOCUMENTS

KR 100486367 B1 4/2005

OTHER PUBLICATIONS

Liao et al., J Biomed Mater Res, 2002, vol. 59, p. 676-681.*
Van de Witte et al., Journal of Polymer Science: Part B: Polymer Physics, 19996, vol. 34, p. 2569-2578.*
Wu et al., J Biomed. Mater. Res., Aug. 2005, vol. 75A, p. 767-777.*
Karageorgiou et al., Biomaterials, Apr. 2005, vol. 26, p. 5474-5491.*
Mikos et al., Polymer, 1994, vol. 35, No. 5, Abstract.*
Hu et al., J. Biomed. Mater. Res. 2002, vol. 59, p. 563-572.*

* cited by examiner

*Primary Examiner*—Leon B Lankford
*Assistant Examiner*—Kade Ariani
(74) *Attorney, Agent, or Firm*—Jones Day

(57) ABSTRACT

There is provided a method of preparing biodegradable dual pore polymer scaffolds, comprising the steps of: maintaining a polymer solution containing a biodegradable polymer, an effervescent mixture of carbonate and organic acid, and solvent at a temperature range of −196° C. to ambient temperature so as to evaporate the solvent and produce a polymer sample; and foaming the polymer sample in a mixed solution of water and alcohol.

According to the present invention, the pore size of the polymer scaffolds can be easily controlled, and biodegradable polymer scaffolds can be more simply prepared compared to conventional methods such as salt leaching technique, phase separation technique or gas foaming technique. Further, since the biodegradable polymer scaffolds prepared according to the present invention have a high surface area and porosity without formation of skin layer, secretion of toxic substances and remnant phenomenon, they can be advantageously used for regenerating almost all living tissues and organs in tissue engineering.

14 Claims, 1 Drawing Sheet

METHOD OF PREPARING BIODEGRADABLE DUAL PORE POLYMER SCAFFOLDS FOR TISSUE ENGINEERING

FIELD OF THE INVENTION

The present invention generally relates to a method of preparing biodegradable dual pore polymer scaffolds for tissue engineering. More particularly, the present invention relates to a simple process of preparing biodegradable dual pore scaffolds for tissue engineering, which have a high surface area and porosity without toxic substance secretion and remains, while being adapted for easy control of pore size.

BACKGROUND OF THE INVENTION

Tissue engineering is a new field that has developed with the progress of science. Tissue engineering involves concepts and techniques from various fields of science such as life science, engineering, medical science and the like. Tissue engineering aims to understand the relationship between the structure and function of a body tissue and producing a substitute for a damaged body tissue or organ for transplantation purposes so as to maintain, improve or restore the function of a human body.

One typical tissue engineering technique comprises the following steps: removing a required tissue from a patient body; isolating a cell from the removed tissue; proliferating the isolated cell; seeding the cell in the biodegradable porous polymer scaffolds; culturing the cell in vitro for a predetermined period; and transplanting the obtained hybrid-type cell/polymer structure into the human body. After the transplantation is achieved, oxygen and nutrients are provided to the transplanted cells in biodegradable porous polymer due to the diffusion of bodily fluids until a blood vessel is newly formed. When the blood vessel is formed, the cells are cultivated and divided in order to form a new tissue and organ. During the formation of new tissue and organ, the polymer scaffolds become degraded and eventually disappear.

Accordingly, in the field of tissue engineering, it is important to prepare a biodegradable porous polymer scaffold that is similar to the body tissue.

In order to be used as a raw material for the polymer scaffolds, the material should properly serve as a matrix or frame so that tissue cells can adhere to the surface of the material and form a tissue in a three-dimensional structure. It should also serve as a middle barrier, which is positioned between a transplanted cell and a host cell. That is, it should be non-toxic and biocompatible such that neither blood coagulation nor inflammatory reaction occurs after the transplantation.

In addition, such material should be biodegradable so that as the transplanted cell properly functions as a tissue, it is completely degraded in vivo within a desired timeframe.

A biodegradable polymer, which is widely used as a raw material for the scaffold, includes polyglycolic acid (PGA), poly(L-lactic acid) (PLLA), poly(D,L-lactic acid) (PDLLA), poly(lactic-co-glycolic acid) copolymer (PLGA), poly(ε-caprolactone) (PCL), polyamino acid, polyanhydride, polyorthoester and their copolymers. However, only PGA, PLLA and PLGA have been approved from the U.S. Food & Drug Administration as biodegradable polymers, which may be used on human bodies. Further, they are used as raw materials for biodegradable porous polymer scaffolds for regeneration within human bodies.

Recently, various attempts were made to prepare a polymer having a porous structure through techniques such as: sol-vent-casting and particulate-leaching technique (see A. G. Mikos et al., Polymer, 35, 1068, 1994) wherein a single crystal NaCl is mixed, dried and dissolved in water; gas foaming technique (see L. D. Harris et al., Journal of Biomedical Materials Research, 42, 396, 1998) wherein a polymer is inflated by using $CO_2$ gas; fiber extrusion and fabric forming process (see K. T. Paige et al., Tissue Engineering, 1, 97, 1995) wherein a polymer fiber is formed as a non-woven fabric to make a polymer mesh; thermally induced phase separation technique (see C. Schugens et al., Journal of Biomedical Materials Research, 30, 449, 1996) wherein a solvent contained in the polymer solution is immersed in a non-solvent to produce porosity; and emulsion freeze-drying method (see K. Whang et al., Polymer, 36, 837, 1995) wherein a polymer solution is mixed with water to form an emulsion, which is then frozen with liquid nitrogen and freeze-dried.

However, with the conventional methods, it is not easy to control the pore size of the scaffold. Further, the surface area and porosity of the resultant polymer scaffolds are comparatively low and the open structures are not formed well between the pores. In addition, they are disadvantageous in that there are occurrences of closed pores on the surface of the scaffolds, the process is comparatively complicated, the gas or toxic substance is secreted during the preparation of scaffolds, and there are remains of salt in the scaffolds.

SUMMARY OF THE INVENTION

It is a primary object of the present invention to provide a method of preparing a biodegradable dual pore polymer scaffold for tissue engineering, which has a high porosity and surface area.

It is another object of the present invention to provide an open cell structure in which the pores are interconnected with each other so as to eliminate the problems associated with secretions of toxic substance, occurrences of salt remains, formation of skin layer on porous scaffold surfaces and the use of complicated process, while being adapted for easy control of pore size.

It is yet another object of the present invention to provide biodegradable dual pore polymer scaffolds, which are prepared in accordance with the above method.

In accordance with one aspect of the present invention, there is provided a process of preparing biodegradable dual pore polymer scaffolds, which comprises the following steps: i) maintaining a polymer solution containing a biodegradable polymer, an effervescent mixture of a carbonate and an organic acid, and a solvent within a temperature range of −196° C. to ambient temperature so as to evaporate the solvent; and ii) adding the polymer sample obtained in step i) to a mixed solution of water and alcohol to effervesce and then drying the resulting substance.

In accordance with another aspect of the present invention, there is provided a biodegradable dual pore polymer scaffold, which is prepared in accordance with the above method.

BRIEF DESCRIPTION OF THE DRAWINGS

The above and other objects and features of the present invention will become apparent from the following description of preferred embodiments given in conjunction with the accompanying drawing, in which.

DETAILED DESCRIPTION OF THE PRESENT INVENTION

Figure 1:
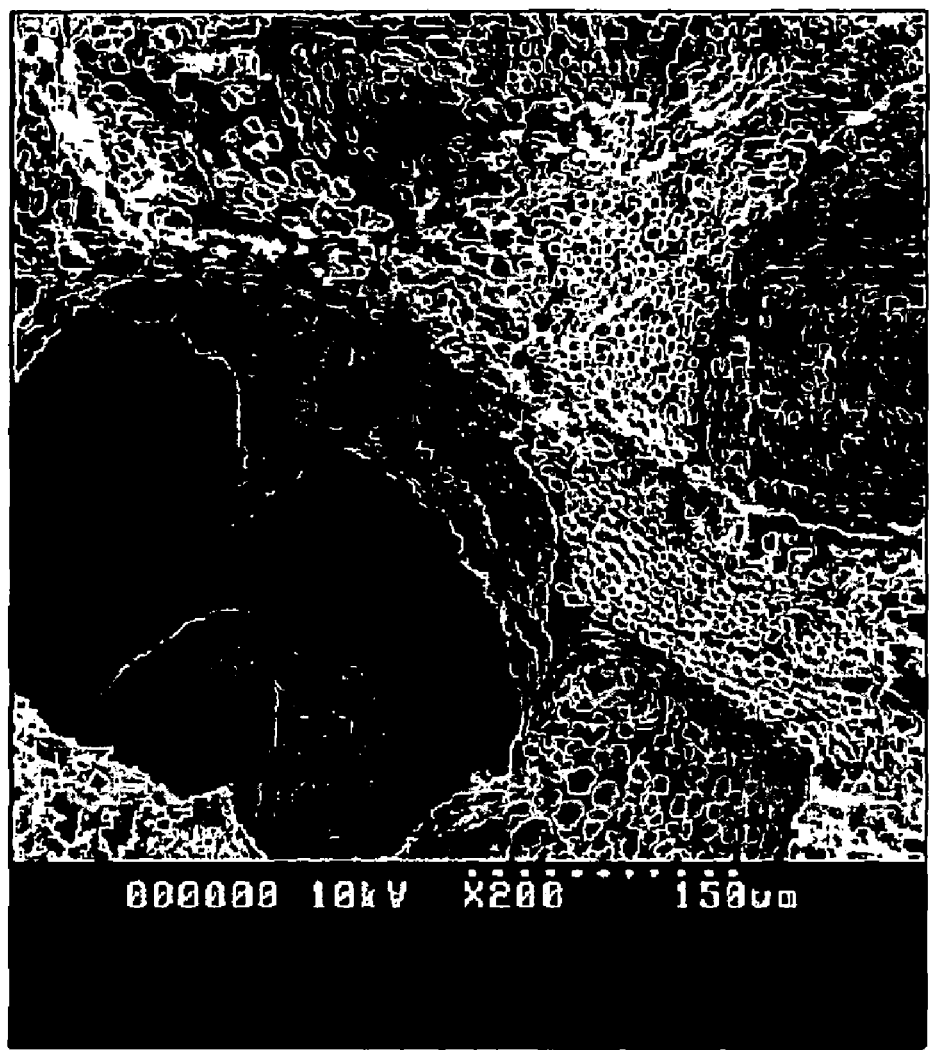
FIG. 1 is a scanning electron microscope (SEM) picture of the external surface of the dual pore PLLA scaffolds, which are prepared in accordance with Example 1 of the present invention.

The method of the present invention is characterized in that the dual pore polymer scaffolds are obtained by directly adding an effervescent mixture to a biodegradable polymer solution. Then, the resulting mixture is dissolved in an effervescent medium such as an aqueous alcohol solution to generate $CO_2$ gas.

The present invention is described below in detail.

In the method of the present invention, dual pores may be formed by: a) forming a large pore using an effervescent mixture, while forming a small pore using a solution containing non-solvent; or b) forming two types (in size) of pores by controlling the particle size of the effervescent mixture.

The method of the present invention, which is for preparing dual pore polymer scaffolds by using an effervescent mixture, is now described in more detail.

In step i), the polymer solution may be obtained through the following steps: providing a solvent/non-solvent mixed solution of a suitable solvent that can dissolve a polymer and a non-solvent, which can not dissolve a polymer but is miscible with the solvent; dissolving a biodegradable polymer therein; adding an effervescent mixture of a carbonate and an organic acid to generate porosity; and uniformly mixing the resulting mixture. Alternatively, the polymer solution may be prepared by: dissolving a biodegradable polymer in a suitable solvent; adding an effervescent mixture of a carbonate and an organic acid to generate dual pore with varying particle sizes; and uniformly mixing the resulting mixture.

In the present invention, the concentration of the polymer solution is preferably from 5 to 15% by weight.

When the polymer solution is prepared according to the first method as described above, methylene chloride, chloroform, carbon tetrachloride, acetone, dioxane, tetrahydrofuran or a mixture thereof may be employed as a solvent depending on the type of the polymer. Further, water, ethanol, methanol, acetone or the like may be employed as a non-solvent for making small pores. The amounts of solvent and non-solvent should be in the range where the latter is miscible with the solvent but cannot dissolve the polymer, preferably having the ratio of solvent to non-solvent in the range from 80:20 to 95:5 by volume.

When the polymer solution is prepared according to the second method, methylene chloride, chloroform, carbon tetrachloride, acetone, dioxane, tetrahydrofuran or the like may be employed as a solvent depending on the type of polymer. Further, it is preferable to use the effervescent mixture wherein the particles for forming a large pore and a small pore are mixed in a weight ratio of 10:1 to 1:1 by weight.

Subsequently, the polymer solution is poured into a frame having a desired shape, which is made of a silicone or Teflon material. Then, it should be maintained within a temperature range of −196° C. to ambient temperature so as to evaporate the solvent contained therein to some extent, thereby fabricating a disk-type polymer sample.

The biodegradable polymer used in the present invention is a non-toxic polymer and is biodegradable in the human body. For example, polyglycolic acid (PGA), poly(L-lactic acid) (PLLA), poly(D,L-lactic acid) (PDLLA), poly(lactic-co-glycolic acid) copolymer (PLGA), poly(ε-caprolactone) (PCL), polyamino acid, polyanhydride, polyorthoester, and their derivatives and copolymers may be used as a biodegradable polymer. However, it should not be limited to the above examples.

Among them, it is preferable to use polyglycolic acid (PGA), poly(L-lactic acid) (PLLA), poly(lactic-co-glycolic acid) copolymer (PLGA) or a mixture thereof, which has been approved from the U.S. Food & Drug Administration as a biodegradable polymer that may be used in the human body. The average molecular weight of the biodegradable polymer is preferably 5,000~2,000,000, and more preferably 10,000~700,000. However, the average molecular weight should not be limited to the above.

The effervescent mixture, which is used in the present invention for forming pores, comprises carbonate and organic acid. The effervescent mixture comprising carbonate and organic acid is harmless to the human body and can be used in a common medicine. Further, it is a solid that is easily dissolved in water and which has a certain size.

Carbonate is preferably selected from the group consisting of sodium bicarbonate, sodium carbonate, ammonium bicarbonate, ammonium carbonate, potassium bicarbonate, potassium carbonate, calcium carbonate and their mixture, which generate carbon dioxide. Further, organic acid is preferably selected from the group consisting of citric acid, tartaric acid, succinic acid, maleic acid, fumaric acid, malonic acid, malic acid, gluconic acid, mucic acid, a certain amino acid and their mixture.

The particle size of the effervescent mixture depends on the use. Typically, 5~500 μm is suitable. The weight ratio of the effervescent mixture to the polymer is preferably 5/1~20/1. In the effervescent mixture, the molar ratio of organic acid to carbonate is preferably controlled in the range of 1:1 or 1:3. In case two or more organic acids are used, the ratio of the organic acids depends on the molar ratio of the carboxyl group.

The disk-type polymer sample, which is obtained in step i), is then subjected to an effervescence (foaming) process. The effervescence (foaming) process is preferably performed in the presence of a mixed solution medium of water and alcohol to remove the residual organic solvent and to lead to immersion of the scaffolds.

Specifically, in step ii), the polymer scaffolds having high dual pores even on the surface thereof may be obtained by the following steps: adding the disk-type polymer sample in an aqueous alcohol solution; foaming it using a physical method; and drying the sample.

Alcohol, which can be used in the mixed aqueous solution, includes, but not limited to, ethanol, methanol and isopropyl alcohol. Its content is preferably from 1 to 95% by weight.

In addition, when $CO_2$ is generated by adding the effervescent mixture to an effervescing medium (i.e., when $CO_2$ is effervescing), a physical method including ultrasonic, microwave or agitation may be conducted. This is to effectively perform effervescence and prevent the lifting of a polymer scaffold due to the attachment of generated gases to the scaffolds.

After completing the effervescing process, the polymer sample is washed with ultra-pure water and dried so as to prepare a biodegradable polymer scaffold. In this respect, in order to minimize the shrinkage phenomenon which may be caused by the rapid evaporation of the excess water and residual organic solvent contained in the porous scaffold, it is preferred that the polymer sample is freeze-dried or vacuum-dried at a room temperature or below a glass transition temperature.

As described above, the method of preparing biodegradable polymer scaffolds of the present invention is advantageous due to the following reasons: the process is simple; the pore size can be easily controlled; the problem caused by the secretion and existence of the toxic substance can be avoided by using a material, which is harmless to the human body; and high efficiency can be achieved.

Further, the biodegradable scaffolds prepared according to the present invention are dual pore scaffolds wherein small pores having a size of 5 to 40 μm are formed on the walls connecting large pores, which have a size of 50 to 500 μm. Such scaffolds have a very large surface area per unit volume as well as a high porosity of 90% or more. Thus, they may be advantageously used in regenerating tissues or organs by tissue engineering since more cells can be seeded per unit area when compared to conventional single pore scaffolds.

The present invention is further described and illustrated in the Examples provided below. However, it should be expressly noted herein that the Examples are not intended to limit the scope of the present invention.

Example 1

A poly(lactic-co-glycolic acid) copolymer (PLGA) containing lactic acid and glycolic acid in the weight ratio of 50:50 and having an average molecular weight of about 100,000 was added to a mixed solution of dioxane and water (85:15 w/w) and uniformly dissolved therein by using a magnetic stirrer to provide a 5% by weight of PLGA solution. Then, the effervescent mixture (size of 200-300 μm) of sodium hydrogen carbonate and citric acid (3:1 in molar ratio) was added thereto so that the weight ratio of the effervescent mixture to PLGA was 20/1, and uniformly mixed therein. The mixed solution was poured into a frame made of silicone material, which has a shape of a donut having a diameter of 8 mm, and followed by placing the same in liquid nitrogen at −196° C. to evaporate the solvent to some extent, thereby obtaining a polymer sample having a disk shape. Then, the polymer sample was added to a mixed aqueous solution of water and ethanol (50:50 w/w) and subjected to foaming for 24 hours after undergoing ultrasonication for 30 seconds. After the foaming stage, the sample was taken out and freeze-dried for 20 hours to provide biodegradable dual pore polymer scaffolds. The overall porosity was about 98% when the porosity of the scaffolds was analyzed by using a mercury porosimetry analyzer.

Then, the outer surface of the obtained dual pore polymer scaffolds was observed by using a scan electron microscopy, of which the result is shown in FIG. 1. As can be seen from FIG. 1, there is almost the same pore shape and distribution through the outer and inner sections. Further, the large pores have a size similar to the particle size (200-300 μm) of the effervescent mixture employed, while the small pores have the size in the range from 5 to 20 μm. Also, there is shown an open cell structure in which pores are interconnected with no formation of skin layer on the outer surface of the scaffolds.

Example 2

Biodegradable dual pore polymer scaffolds were prepared according to the same process as described in Example 1. However, poly (L-lactic acid) (PLLA) having an average molecular weight of about 2,000,000 was dissolved in dichloromethane to obtain a 13% by weight of PLLA solution. Further, an effervescent mixture (3:1 w/w ratio of 200-300 μm to 5-30 μm of particle size) of sodium carbonate and citric acid (1:1 in molar ratio) was added so that the weight ratio of the effervescent mixture to PLLA was 5/1. After foaming, vacuum drying was performed at 40° C. The overall porosity of the scaffolds thus prepared was about 96%.

Then, the outer surface of the obtained dual pore polymer scaffolds was observed by using a scan electron microscopy, of which the result was similar to that of FIG. 1. That is, the pore shape and distribution of outer surface and inner cross-section of the scaffolds are almost identical. Also, the size of large pores is similar to the particle size (200-300 μm) of the effervescent mixture employed, while the small pores have the size in the range from 5 to 30 μm. Further, there is shown an open structure in which the pores are interconnected with no formation of skin layer on the outer surface of the scaffolds.

Example 3

Biodegradable dual pore polymer scaffolds were prepared according to the same process as described in Example 1. However, poly(lactic-co-glycolic acid) copolymer (PLGA) (75:25 w/w) having an average molecular weight of about 20,000 was dissolved in a mixed solution of acetone and ethanol (90:10 w/w) to obtain a 8% by weight of PLGA solution. The temperature allowed was −70° C. An effervescent mixture (300-400 μm in size) of ammonium hydrogen carbonate and tartaric acid was added. After foaming, vacuum drying was performed at ambient temperature. The overall porosity of the scaffolds thus prepared was about 93%.

Then, the outer surface of the obtained dual pore polymer scaffolds was observed by using a scan electron microscopy, of which the result was similar to that of Example 1. Further, the pore shape and distribution of outer surface and inner cross-section of the scaffolds are almost identical. Also, the size of large pores is similar to the particle size (300-400 μm) of the effervescent mixture employed, while the small pores have a size in the range from 5 to 20 μm. Further, there is shown an open structure in which the pores are interconnected with no formation of skin layer on the outer surface of the scaffolds.

Example 4

Biodegradable dual pore polymer scaffolds were prepared according to the same process as described in Example 2. However, poly(lactic-co-glycolic acid) copolymer (PLGA) (85:15 w/w) having an average molecular weight of about 220,000 was dissolved in chloroform to obtain a 10% by weight of PLGA solution. Also, a mixture of sodium hydrogen carbonate and tartaric acid having a weight ratio of 1:1 (10:1 w/w ratio of 400-500 μm to 10-40 μm in particle size) was employed as the effervescent mixture. The overall porosity of the scaffolds thus prepared was about 90%.

Then, the outer surface of the obtained dual pore polymer scaffolds was observed by using a scan electron microscopy, of which the result was similar to that of Example 2. Further, the pore shape and distribution of outer surface and inner cross-section of the scaffolds are almost identical. Also, the size of the dual pores is similar to the particle size (400-500 μm and 10-40 μm) of the effervescent mixture employed. Additionally, there is shown an open structure in which the pores are interconnected with no formation of skin layer on the outer surface of the scaffolds.

Example 5

Biodegradable dual pore polymer scaffolds were prepared according to the same process as described in Example 1. However, poly(D,L-lactic acid) (PDLLA) having an average molecular weight of about 17,500 was dissolved in a mixed solution of chloroform and acetone (95:5 w/w) to obtain a 8% by weight of PDLLA solution. The temperature allowed was ambient temperature. An effervescent mixture of ammonium carbonate and succinic acid (100-200 μm in size) was used. Also, a mixed solution of water and ethanol was used as the foaming solution. The overall porosity and results from SEM analysis were similar to those described in Example 1.

Example 6

Biodegradable dual pore polymer scaffolds were prepared according to the same process as described in Example 2. However, poly(ε-caprolactone) having an average molecular weight of about 100,000 was dissolved in tetrahydrofuran to obtain a 7% by weight of poly(ε-caprolactone) solution. An effervescent mixture of potassium hydrogen carbonate and maleic acid (1:1 w/w ratio of 100-200 μm to 5-20 μm in particle size) was used. Also, a mixed solution of water and ethanol (95:5 v/v) was used as the foaming solution. During the foaming stage, microwave radiation was carried out. The overall porosity and results from SEM analysis were similar to those described in Example 2.

Example 7

Biodegradable dual pore polymer scaffolds were prepared according to the same process as described in Example 1. However, a copolymer of glycolic acid and ε-caprolactone (50:50 w/w) having an average molecular weight of about 220,000 was dissolved in a mixture of dioxane and methanol (80:20 v/v) to obtain a 15% by weight of the copolymer solution. An effervescent mixture of potassium carbonate and mucic acid was used. Also, a mixed solution of water and methanol (50:50 v/v) was used as the foaming solution. The overall porosity and results from SEM analysis were similar to those described in Example 1.

Example 8

Biodegradable dual pore polymer scaffolds were prepared according to the same process as described in Example 1. However, polyorthoester having an average molecular weight of about 200,000 was dissolved in chloroform to obtain an 11% by weight of polyorthoester solution. Also, an effervescent mixture of calcium carbonate and aspartic acid was used. The overall porosity and results from SEM analysis were similar to those described in Example 1.

Example 9

Biodegradable dual pore polymer scaffolds were prepared according to the same process as described in Example 1. However, polyanhydrides having an average molecular weight of about 100,000 and an effervescent mixture of sodium hydrogen carbonate and glutamic acid were used. The overall porosity and results from SEM analysis were similar to those described in Example 1.

When the biodegradable dual pore polymer scaffolds prepared according to the method of the present invention is observed by scan electron microscopy, both inner and outer sides thereof have uniform pore size and distribution. As to the pore size, when prepared through process a), large pores have similar particle size to those of the effervescent mixture employed, while the size of small pores ranges from 5 to 20 μm. Further, when prepared through process b), large pores have similar particle size to those of the effervescent mixture employed for forming the porosity, while the size of small pores ranges from 5 to 40 μm. In particular, when the scaffolds are prepared through process b), it is advantageous in that small pores can be formed at a desired size.

In addition, the scaffolds prepared according to the present invention shows three-dimensional porosity of open structure interconnected between the pores without exhibiting no formation of skin layer of outer surface. Also, the overall porosity analyzed by using a mercury porosimetry analyzer is very high (i.e., in the range from about 90 to 98%).

The process of the present invention comprises obtaining polymer pieces from a polymer solution containing biodegradable polymer and effervescent mixture, foaming the resultant mixture in a mixed aqueous solution of water and alcohol, and drying the mixture. Thus, polymer scaffolds can be more simply prepared with easier control of the pore size when compared to the conventional methods.

The polymer scaffolds prepared according to the present invention is dual pore polymer scaffolds wherein large pores of 50-500 μm in size and small pores of 5-40 μm in size on the wall connecting them are formed. Such scaffolds have high porosity of 90% or more and comprise open structures between the pores, as well as having very high surface area per unit volume. Through such dual pore scaffolds, cell growth is guided to enable surface patterning. Thus, they may be advantageously used in artificially regenerating almost all damaged tissues or organs of a body by tissue engineering since there is no formation of skin layer on the surface, no secretion of detrimental substances or occurrence of remnant, and more cells can be seeded per unit area when compared to conventional unipore scaffolds.

While the present invention has been described with respect to the above specific embodiments, it should be recognized that various modifications and changes may be made to the present invention by those skilled in the art which also fall within the scope of the invention as defined by the appended claims.

What is claimed is:

1. A method of preparing a biodegradable dual pore polymer scaffold, the method comprising:
   i) preparing a polymer solution by dissolving a biodegradable polymer in a mixture of an organic solvent capable of dissolving the biodegradable polymer and a non-solvent that is miscible with the organic solvent but that is incapable of dissolving the biodegradable polymer, adding an effervescent mixture of a carbonate and an organic acid thereto, and mixing the resulting mixture, wherein the effervescent mixture comprises particles having a particle size in the range from 5 μm to 40 μm for forming small pores and particles having a particle size in the range from 100 μm to 500 μm and, wherein the organic solvent is selected from the group consisting of methylene chloride, chloroform, carbon tetrachloride, acetone, dioxane, tetrahydrofuran, dichloromethane, and mixtures thereof, and wherein the non-solvent is selected from the group consisting of water, ethanol, methanol, and mixtures thereof; then
   ii) forming a polymer sample by drying the polymer solution obtained in step i) and evaporating said mixture of organic solvent and the non-solvent, thereby forming a plurality of small pores in the polymer sample; and then
   iii) adding said polymer sample obtained in step ii) to a mixed solution of water and alcohol and then drying the resulting substance, the mixed solution causing the effervescent mixture in the polymer to effervesce and form a plurality of large pores in the polymer sample, thereby providing a biodegradable dual pore polymer scaffold with small pores interconnected with the large pores.

2. The method of claim 1, wherein the biodegradable polymer is selected from the group consisting of polyglycolic acid (PGA), poly(L-lactic acid) (PLLA), poly(D,L-lactic acid) (PDLLA), poly(lactic-co-glycolic acid) copolymer (PLGA), poly(ε-caprolactone) (PCL), polyamino acids, polyanhydrides, polyorthoesters, and derivatives and copolymers thereof.

3. The method of claim 1, wherein an average molecular weight of the biodegradable polymer is in the range from 5,000 to 2,000,000.

4. The method of claim 1, wherein a concentration of the polymer solution is in the range from 5 to 15% by weight.

5. The method of claim 1, wherein the weight ratio of the organic solvent to the non-solvent is in the range from 80:20 to 95:5.

6. The method of claim 1, wherein the effervescent mixture comprises a carbonate and an organic acid in the molar ratio ranging from 1:1 to 1:3.

7. The method of claim 1, wherein the carbonate is selected from the group consisting of sodium hydrogen carbonate, sodium carbonate, ammonium hydrogen carbonate, ammonium carbonate, potassium hydrogen carbonate, potassium carbonate, calcium carbonate and mixtures thereof.

8. The method of claim 1, wherein the organic acid is selected from the group consisting of citric acid, tartaric acid, succinic acid, maleic acid, fumaric acid, malonic acid, malic acid, gluconic acid, mucic acid and amino acids.

9. The method of claim 1, wherein the effervescent mixture has a particle size in the range from 5 to 500 μm.

10. The method of claim 1, wherein the effervescent mixture and the biodegradable polymer are employed in a weight ratio from 5:1 to 20:1.

11. The method of claim 1, wherein the mixed solution of water and alcohol comprises from 1 to 95% by weight of alcohol.

12. The method of claim 1, wherein an alcohol of the mixed solution of water and alcohol is selected from the group consisting of ethanol, methanol, isopropyl alcohol and mixtures thereof.

13. The method of claim 1, wherein the effervesce process of step iii) is performed using a physical method selected from the group consisting of ultrasonication, microwave radiation and agitation.

14. The method of claim 1, wherein drying is performed by freeze-drying or vacuum-drying at a temperature ranging from ambient temperature to glass transition temperature of the resulting scaffolds.

* * * * *